(12) United States Patent
Memtsoudis

(10) Patent No.: US 10,960,176 B2
(45) Date of Patent: Mar. 30, 2021

(54) MULTI-CATHETER INFUSION SYSTEM AND METHOD THEREOF

(71) Applicant: Hospital for Special Surgery, New York, NY (US)

(72) Inventor: Stavros Memtsoudis, Rumson, NJ (US)

(73) Assignee: Hospital for Special Surgery, New York, NY (US)

( * ) Notice: Subject to any disclaimer, the term of this patent is extended or adjusted under 35 U.S.C. 154(b) by 0 days.

(21) Appl. No.: 15/536,348

(22) PCT Filed: Dec. 21, 2015

(86) PCT No.: PCT/US2015/067080
§ 371 (c)(1),
(2) Date: Jun. 15, 2017

(87) PCT Pub. No.: WO2016/100970
PCT Pub. Date: Jun. 23, 2016

(65) Prior Publication Data
US 2017/0361063 A1    Dec. 21, 2017

Related U.S. Application Data

(60) Provisional application No. 62/094,514, filed on Dec. 19, 2014.

(51) Int. Cl.
*A61M 25/04* (2006.01)
*A61M 25/00* (2006.01)
(Continued)

(52) U.S. Cl.
CPC ........ *A61M 25/0026* (2013.01); *A61M 5/158* (2013.01); *A61M 5/16804* (2013.01);
(Continued)

(58) Field of Classification Search
CPC .......... A61M 25/0071; A61M 25/0082; A61M 25/0084; A61J 15/0069; A61J 15/003; A61J 15/0034; A61J 15/0046; A61J 15/0057
See application file for complete search history.

(56) References Cited

U.S. PATENT DOCUMENTS 5,002,059 A * 3/1991 Crowley .................. A61B 8/12
600/466
5,607,462 A    3/1997 Imran
(Continued)

FOREIGN PATENT DOCUMENTS

WO    0112158 A1    2/2001
WO    2007079152 A2    7/2007
(Continued)

OTHER PUBLICATIONS

International Search Report for PCT/US2015/067080 dated Feb. 5, 2016.
(Continued)

*Primary Examiner* — Nathan R Price
*Assistant Examiner* — Courtney B Fredrickson
(74) *Attorney, Agent, or Firm* — Kim IP Law Group LLC

(57) ABSTRACT

A multi-catheter infusion system and method for the localized delivery of medications while minimally affecting patient mobility for an extended period of time. The multi-catheter infusion system includes a cannula and a plurality of catheters. The cannula includes a first end for connecting to a drug delivery system and a second end for connecting to the plurality of catheters. The plurality of catheters are in fluid communication with the cannula for delivering a drug to a target area of a patient. Each catheter includes a multi-orifice distal end.

18 Claims, 7 Drawing Sheets

(51) Int. Cl.
*A61M 5/168* (2006.01)
*A61M 39/02* (2006.01)
*A61M 5/158* (2006.01)
*A61M 25/06* (2006.01)
*A61M 25/02* (2006.01)

(52) U.S. Cl.
CPC .... *A61M 25/0084* (2013.01); *A61M 39/0247* (2013.01); *A61M 25/04* (2013.01); *A61M 25/065* (2013.01); *A61M 2025/0286* (2013.01); *A61M 2039/0264* (2013.01); *A61M 2039/0282* (2013.01); *A61M 2205/3331* (2013.01)

(56) References Cited

U.S. PATENT DOCUMENTS

| | | | |
|---|---|---|---|
| 5,611,338 A | 3/1997 | Gallup et al. | |
| 6,159,196 A | 12/2000 | Ruiz | |
| 6,280,413 B1 | 8/2001 | Clark et al. | |
| 6,638,263 B1 | 10/2003 | Theeuwes et al. | |
| 7,022,107 B1 | 4/2006 | Christensen et al. | |
| 7,087,040 B2 | 8/2006 | McGuckin, Jr. et al. | |
| 7,510,552 B2 | 3/2009 | Lebel et al. | |
| 7,850,656 B2* | 12/2010 | McKay | A61B 17/3478 604/173 |
| 8,062,247 B2 | 11/2011 | Abe et al. | |
| 2002/0193751 A1 | 12/2002 | Theeuwes et al. | |
| 2003/0045866 A1 | 3/2003 | Petersen | |
| 2005/0059930 A1 | 3/2005 | Garrison et al. | |
| 2006/0173440 A1 | 8/2006 | Lamson et al. | |
| 2007/0250035 A1 | 10/2007 | El-Nounou et al. | |
| 2008/0172012 A1* | 7/2008 | Hinidunna-Lokuge | A61M 5/3291 604/272 |
| 2008/0312611 A1* | 12/2008 | Racz | A61M 5/3291 604/272 |
| 2009/0018638 A1* | 1/2009 | Shirley | A61M 25/0084 623/1.14 |
| 2009/0082758 A1* | 3/2009 | Gill | A61M 5/14276 604/891.1 |
| 2013/0253448 A1* | 9/2013 | Baron | A61M 5/3291 604/272 |
| 2013/0296699 A1* | 11/2013 | Deckman | A61B 8/445 600/439 |
| 2014/0039315 A1* | 2/2014 | Davies | A61M 25/0108 600/439 |
| 2015/0018758 A1 | 1/2015 | John | |

FOREIGN PATENT DOCUMENTS

| | | |
|---|---|---|
| WO | 2012/135224 | 10/2012 |
| WO | 2012135224 A1 | 10/2012 |
| WO | 2015117025 A1 | 8/2015 |

OTHER PUBLICATIONS

International Preliminary Report on Patentability for PCT/US2015/067080 dated Jan. 31, 2017.
Written Opinion of the International Searching Authority dated Feb. 5, 2016.
European Search Report dated Mar. 22, 2019 in Application No. 15871273.7, 10 pages.
Provisional Opinion Report Accompanying the Partial Search Result dated Jul. 9, 2018 in Application No. 15871273.7, 9 pages.
Supplemental European Search Report dated Mar. 12, 2019 in Application No. EP 15871273, 4 pages.
Supplemental European Search Report dated Jun. 27, 2018 2019 in Application No. EP 15871273, 6 pages.

\* cited by examiner

MULTI-CATHETER INFUSION SYSTEM AND METHOD THEREOF

CROSS-REFERENCE TO RELATED APPLICATIONS

This application is a United States national phase application under 35 U.S.C. § 371 of International Application No. PCT/US2015/067080 filed Dec. 21, 2015, which claims the benefit of U.S. Provisional Patent Application No. 62/094,514 filed Dec. 19, 2014, the entire disclosures of which are hereby incorporated by reference in their entirety.

BACKGROUND OF THE INVENTION

The present invention relates to a multi-catheter infusion system used for the administration of local anesthetics or other fluids (including but not limited to antibiotics or pain relief drugs) to a patient. In particular, the present invention provides a multi-catheter infusion system and method thereof for the localized delivery of e.g., medications over extended periods of time and near a wound site while minimally affecting patient mobility over an extended period of time.

Current methods of drug delivery to a wound site use multiple, divided injections of local anesthetics into tissue surrounding the wound, such as periarticular injections after total joint arthroplasty, and have been shown to improve post-operative pain control and facilitate mobility. These injections are traditionally performed by surgeons at the end of the procedure, are easy to perform and require little training. However, such methods are disadvantageous in that they have limited time of action, which in part depends on the local anesthetic used.

Although recently longer acting formulations of local anesthetics have become available, their efficacy is still unknown, and little is known at this time regarding infection risk, potential for neuro and tissue toxicity or any other long-term side effects. Further, once injected the length of action, duration, and strength of the anesthetic cannot be controlled or adjusted. Moreover, the type of infusion cannot be adjusted.

Thus, there is still a need to address the foregoing limitations of conventional drug delivery systems, such as limited time of action and the need for multiple injections into tissue surrounding the wound. Such a need is satisfied by the present invention.

BRIEF SUMMARY OF THE INVENTION

In accordance with a preferred embodiment, the present invention provides a multi-catheter infusion system that includes a cannula having a first end for connecting to a drug delivery system and a second end opposite the first end. The system further includes a plurality of catheters attached to the second end in fluid communication with the cannula for delivering a drug to a target area of a patient. Each catheter includes a multi-orifice distal end. The second end of the cannula includes a regulator. The regulator can be a flow regulator or a pressure regulator. The cannula is flexible and further includes a detachable needle for facilitating the positioning of the multi-catheter infusion system. Additionally, the cannula has a cross-sectional diameter greater than an overall diameter of the plurality of catheters.

The plurality of catheters are attached to the second end downstream the regulator. Moreover, the plurality of catheters are about 5-10 inches in length and each catheter is about 28-15 gauge in diameter. Each of the plurality of catheters may alternatively be configured to have a cross-sectional diameter sufficient to draw fluid from the cannula by capillary action. The distal end of each of the plurality of catheters has a closed distal face. The distal end of the each of the plurality of catheters further includes a needle that is detachable from the catheter. Further, the distal end of each of the plurality of catheters includes a weakened portion for detaching the needle from each catheter. Furthermore, the multi-orifices of the distal end extend about 0.1-2 inches.

In accordance with another preferred embodiment, the present invention provides a method for delivery of a drug to a patient. The method includes inserting a multi-catheter infusion system having a cannula and a plurality of catheters extending from the cannula through a patient's skin such that the plurality of catheters are positioned underneath the skin, positioning each of the plurality of catheters to a predetermined location, and delivering a drug to the patient through the multi-catheter infusion system. Further, the step of inserting the multi-catheter infusion system through the patient's skin includes detaching a guide needle from the cannula.

The method further comprises securing a distal end of each of the plurality of catheters to a desired location by passing the distal end through soft tissue at the desired location. Moreover, the distal end of each of the plurality of catheters includes a needle. Further, the method comprises detaching the needle from each of the plurality of catheters after passing the distal end through soft tissue at the desired location. Furthermore, the method comprises withdrawing the multi-catheter infusion system from the patient by directly pulling the multi-catheter infusion system through the patient's skin.

In accordance with an aspect, the present invention provides a multi-catheter infusion system having an external cannula that would be connected to a medication delivery system on one side and the other side with multiple catheters. The placement of catheters, that would deliver drug to the target area under the skin of the patient under direct vision, would be facilitated by an attached hook-shaped needle that is detached after positioning. This leaves the multi-orifice, closed tip catheter in situ. A regulator is attached to gauge the infusion pressure and regulate the amount of fluid entering the patient.

In accordance with another aspect, the multi-catheter infusion system includes an external, larger bore cannula that would be connected to a medication delivery system such as a pump. The placement of this portion through the skin of the patient would be facilitated by an attached needle that is being cut off after placement. A universal connector connecting this portion of the cannula to an external drug delivery system will then be attached. The opposite end of this cannula would end in a hub giving rise to multiple smaller catheters that can be placed individually at various desired locations in the surgical field under direct vision. Placement of catheters (as well as the cannula) will be facilitated by needles at the end of the catheters that can be cut after placement. The distal part of the cannula including the transition area to the smaller catheters would be positioned under the level of the skin as to represent only one entry site into the patient's body. Different versions varying in the length and number of the catheters could allow for the placement according to the area to be covered. Catheters will be multi-orifice at their distal end to allow the infusion to be disbursed effectively. The multi-catheter infusion system will be removable easily as there is no active anchoring.

The multi-catheter infusion system can be implanted in the patient during the surgical procedure at the point immediately before wound closure. The surgeon would choose a convenient skin exit site for the external cannula and pass the needle attached to the cannula from the inside of the wound through the skin to the outside in a manner that the regulator and attached plurality of catheters remain under the skin. The needle attached at the end of the cannula is cut and a universal connector for eventual connection to a drug delivery system is attached. Under the direct field of vision, the surgeon places the catheters at the desired locations of drug delivery. In order to accomplish this, the hook-shaped needle at a distal end of each catheter is placed with a needle driver in the desired location. Specifically, the needle is driven through the desired tissue and the cannula is subsequently pulled through. Once anchored in the desired location, the needle tip is cut within the distal, solid portion thus yielding a closed-tip multi-orifice catheter. This step is repeated for each additional catheter until each of the plurality of catheters is anchored to the tissue.

At this point, the surgeon may choose to inject a small amount of local anesthetic or other desired medications and observe the distribution of fluid under direct vision, to inspect that everything is operational. The wound is subsequently closed in a routine manner. The cannula exit site is dressed in a sterile fashion as routinely done during similar routine surgical procedures. Alternatively, the surgeon may choose to suture the cannula in place or leave the cannula unanchored (i.e., kept in place by tissue anchoring alone). After completion of the surgical procedure, the external cannula is connected to a drug delivery system or infusion pump by a nurse or an assistant. The multi-catheter infusion system may remain in place as long as desired. Typically, this period can be about 1-4 days or longer, with regular daily inspections at the insertion site for signs of infection. Additionally, the infusion can be titrated according to the patient's needs, per a doctor's instructions. Finally, when removal of the multi-catheter infusion system is desired the cannula is simply pulled through the insertion site with steady traction.

The present invention provides an improved multi-catheter infusion system that would allow for targeted administration of local anesthetics or other drug fluids, for example to provide prolonged and titratable analgesia while minimally affecting patient mobility. Periarticular analgesia and wounds covering large areas may be especially amenable to such a technique.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Reference will now be made in detail to the preferred embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Figure 1:
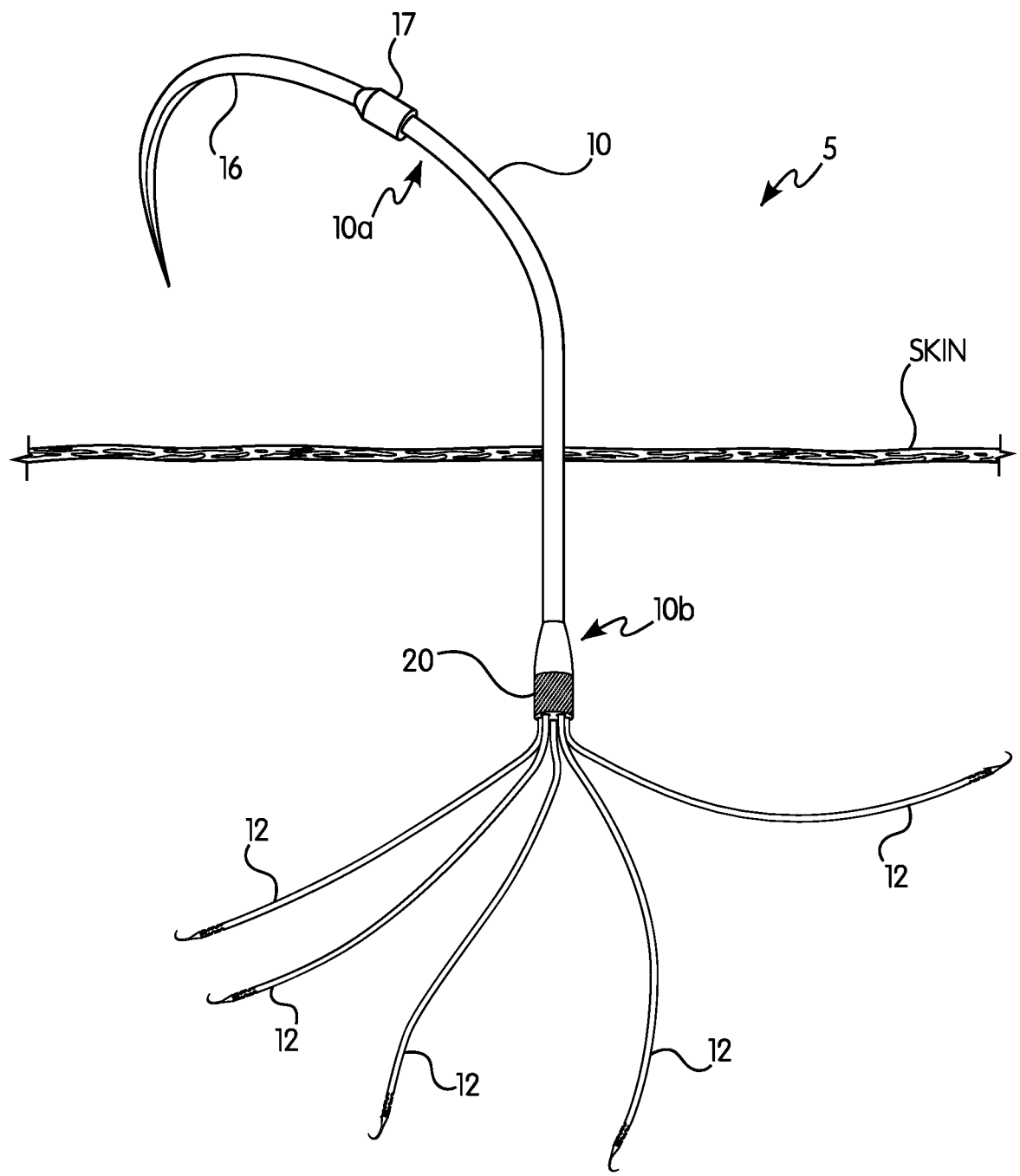
FIG. 1 is a perspective view of a multi-catheter infusion system in accordance with a preferred embodiment of the present invention.
Figure 2:
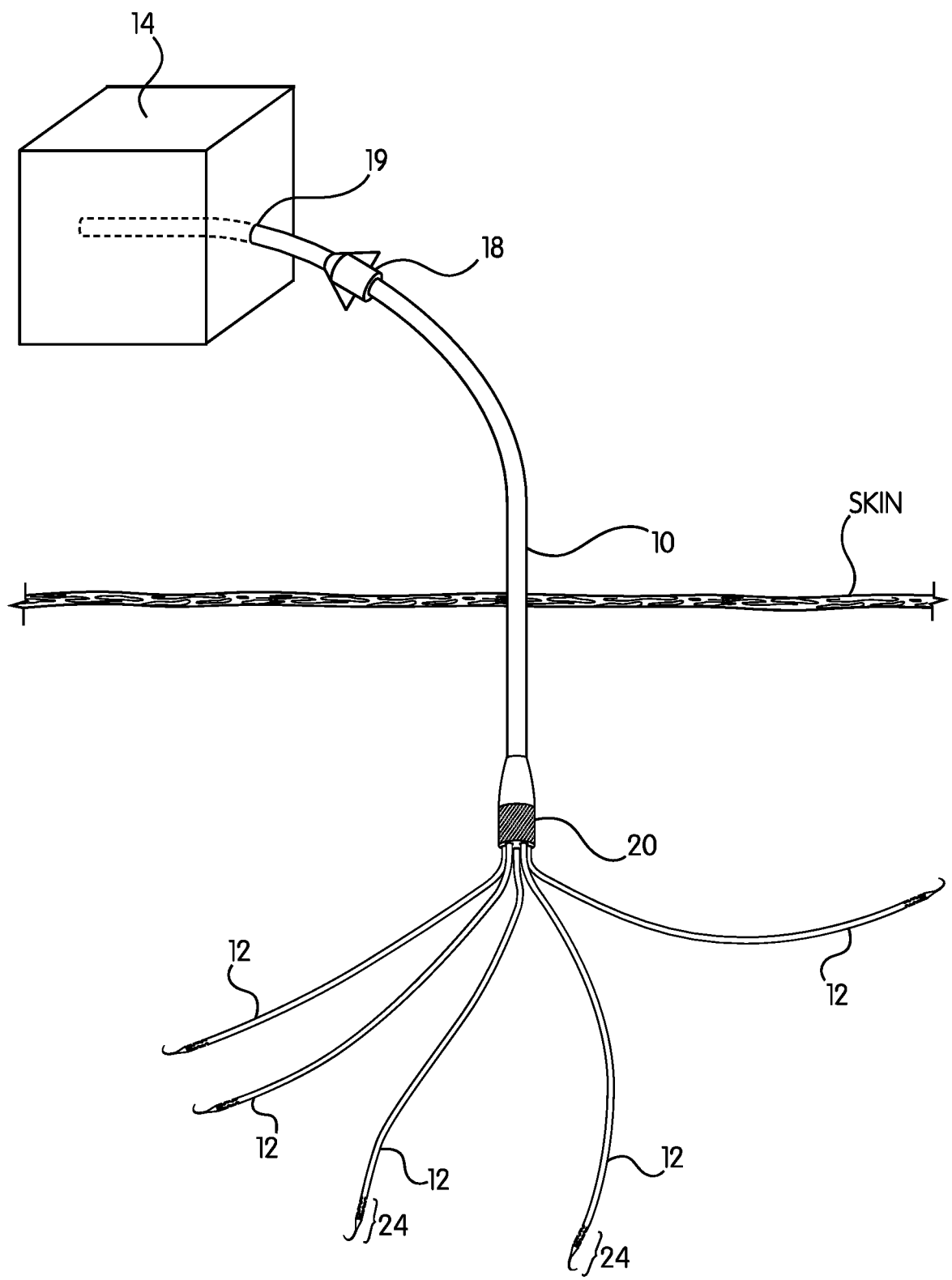
FIG. 2 is another perspective view of the multi-catheter infusion system of FIG. 1 connected to a drug delivery system.

In accordance with a preferred embodiment, the present invention provides a multi-catheter infusion system 5 as configured in FIGS. 1 and 2. The multi-catheter infusion system 5 includes a cannula 10 and a plurality of catheters 12. The cannula 10 includes a first end 10a for connecting to a drug delivery system 14 and a second end 10b opposite the first end.

The cannula 10 can be any cannula suitable for its intended purpose. For example, the cannula can be any tubular or elongated vessel member for delivering fluids. Preferably, the cannula 10 is configured as a flexible elongated tubular member. The cannula 10 is also preferably configured to have a cross-sectional diameter greater than an overall diameter or width of the plurality of catheters 12 when collectively assembled. The cannula can be about 4-40 inches in length and preferably about 6-24 inches in length and more preferably about 8-18 inches in length.

The cannula 10 can be formed from any suitable material, such as silicone, latex, a plastic e.g., polyurethane, polyethylene, polyvinylchloride, polypropylene, polytetrafluoroethylene and nylon, and the like.

The cannula 10 includes a guide needle 16 for facilitating the positioning of the multi-catheter infusion system 5. The guide needle 16 is attached to the first end 10a of the cannula 10. As shown, the guide needle 16 is preferably hook shaped, but can alternatively be any shape suitable for facilitating placement of the cannula 10 through the patient's skin. The guide needle 16 is also configured to be detachable from the cannula 10. For example, the guide needle 16 can be detachably connected via a pressure fit hub, a luer fitting, a luer adapter 17, and the like.

The multicatheter infusion system also includes a universal adapter 18 for attaching to the first end 10a of the cannula 10 after the guide needle is removed from the cannula. The universal adapter 18 can be e.g., a luer adapter, a luer fitting, a hub and the like.

The drug delivery system 14 can be any drug delivery system capable of delivering fluid to the multi-catheter infusion system. For example, the drug delivery system can be a pump, a syringe, an IV bag, etc. The drug delivery system can also be a stationary or portable device. The drug delivery system 14 is capable of delivering a drug e.g., an analgesic, anti-inflammatory agents, antibiotics, nutrients, medications, hormones and the like, to the multi-catheter infusion system. In an aspect of the present embodiment, elution of the drug is preferably delivered at a pressure of 15-25 mmHg.

As shown in FIG. 2, the drug delivery system 14 includes a port 19 for connecting to the cannula 10 via the universal adapter 18. Such drug delivery systems applicable to the present multi-catheter infusion system are known in the art and therefore a further detailed description of their structure, function and operation is not necessary for a complete understanding of the present invention.

The plurality of catheters 12 is attached to the second end 10b of the cannula 10 opposite the first end 10a. The plurality of catheters 12 is in fluid communication with the cannula 10 for delivering a fluid e.g., a drug to a target area of a patient. Each catheter 12 includes a multi-orifice distal end 24.

In accordance with an aspect of the present embodiment, the second end 10b of the cannula 10 includes a regulator 20 for regulating the fluid flowing through the cannula 10 and reaching the plurality of catheters 12. The regulator 20 can be a pressure regulator 20' (FIG. 7B) or a flow regulator 20" (FIG. 7A).

Figure 7A:
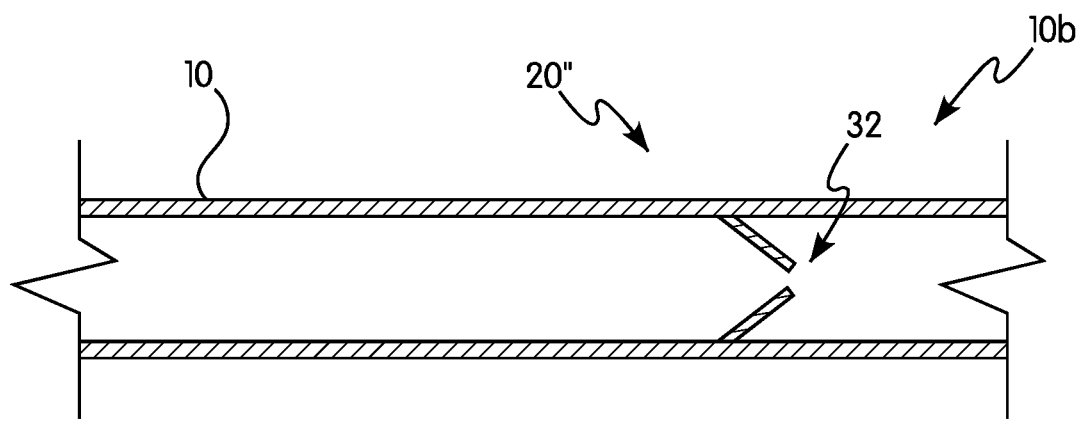
FIG. 7A is a partial cross-sectional view of a flow regulator applicable to the multi-catheter infusion system of FIG. 1.

FIG. 7A illustrates the regulator 20 configured as a flow regulator 20" having a valve 32 for regulating the flow of fluid regulation through the cannula. Additional flow regulators applicable to the present embodiment are disclosed in U.S. Pat. Pub. Nos. 2015/0018758 and 2002/0193751, the entire disclosures of which are hereby incorporated by reference in their entirety for all purposes. Additionally, applicable flow regulator to the present embodiment include e.g. the Harion™ dial flow regulator by Harsonia Healthcare PVT LTD. of Udyog Vihar, Gurgaon, Haryana, India and the STAT 2® IV Gravity Flow controller by CONMED of Utica, N.Y.

Figure 7B:
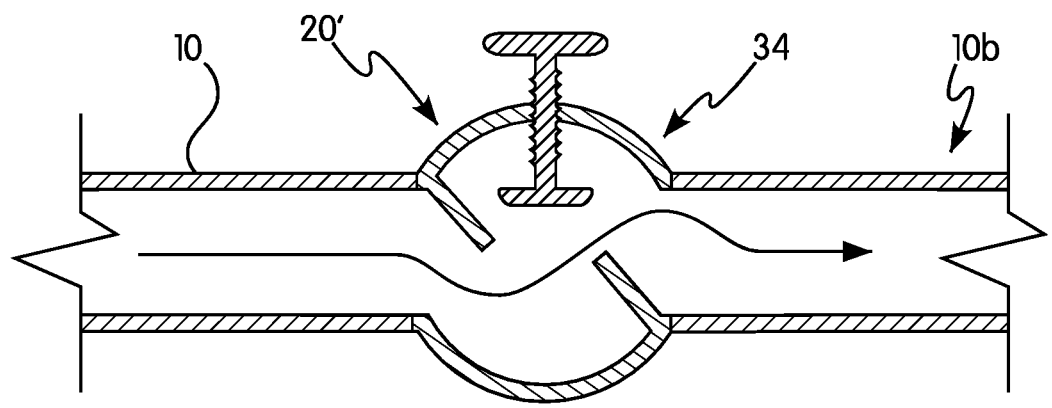
FIG. 7B is a partial cross-sectional view of a pressure regulator applicable to the multi-catheter infusion system of FIG. 1.

FIG. 7B illustrates the regulator 20 configured as a pressure regulator 20' having a globe valve 34 configuration. Alternatively, the pressure regulator 20" can be configured as any other pressure regulator suitable for cannulas or tubing, as readily known in the art.

Figure 3:
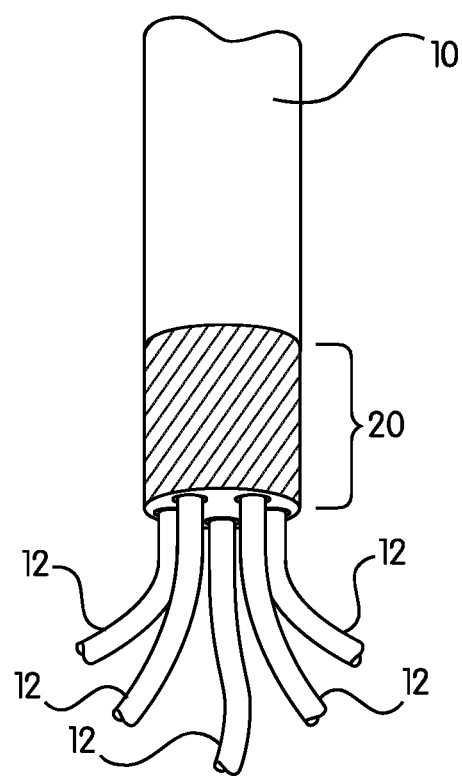
FIG. 3 is an enlarged partial perspective view of the multi-catheter infusion system of FIG. 1.

Referring to FIG. 3, the regulator 20 can be sized to have an overall diameter matching or the same as the cannula 10, so as to easily remove the multi-catheter infusion system through a patient's skin. Alternatively, the regulator can be sized to have a diameter differing from the cannula, e.g., larger, than the cannula, as shown in FIG. 2, with a tapered portion to facilitate removal of the multi-catheter infusion system through a patient's skin.

The plurality of catheters 12 are preferably attached to the second end of the cannula 10 downstream the regulator 20. The plurality of catheters 12 can be any catheter suitable for its intended purpose. For example, each of the plurality of catheters 12 can be any tubular member on elongated vessel for delivering fluids. Preferably, each catheter is configured as a flexible elongated tubular member.

FIG. 1 illustrates the multi-catheter infusion system having five catheters attached to the cannula 10. However, the number of catheters attached to the cannula can be more or less than five, for example, 2, 3, 4, 6, 7, 8, 9, 10 or more catheters.

The catheters 12 can be formed from any suitable material, such as silicone, latex, a plastic e.g., polyurethane, polyethylene, polyvinylchloride, polytetrafluoroethylene, polypropylene, nylon, and the like.

Preferably, each of the plurality of catheters 12 is about 28-15 gauge in diameter. In every configuration, the diameter of each of the plurality of catheters 12 is less than the diameter of the cannula 10. Collectively, the plurality of catheters 12 have an overall diameter or width when assembled together that is less than a cross-sectional diameter of the cannula 10. Each of the plurality of catheters 12 is also preferably configured to have a length from about 5-10 inches but can be more or less than 5-10 inches such as 2, 4, 12, 14, 16, 18, 20, 22 and 24 or more inches, depending on the type of wound, location of the wound, and size of the wound area. Additionally, each of the plurality of catheters can be configured to have the same overall length or varying lengths e.g., 5 inches, 7 inches, and 9 inches.

Further, in accordance with another aspect, each of the plurality of catheters 12 can be configured to have a cross-sectional diameter sufficient to draw fluid from the cannula 10 by capillary action. For example, when the drug is traveling to the cannula 10, the narrower diameter of the catheters will cause the drug to flow through the plurality of catheters under capillary action as opposed to positive pressure forcing fluid flow through the catheters.

Figure 4A:
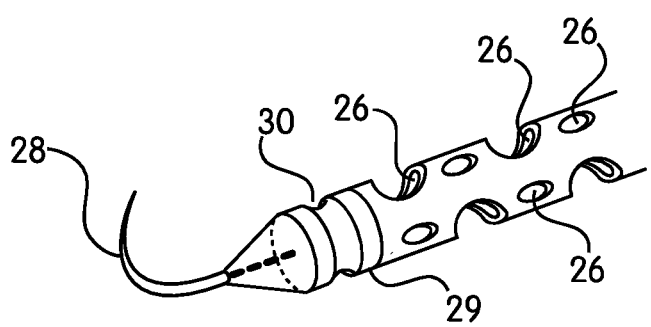
FIG. 4A is an enlarged partial perspective view of a distal end of an individual catheter of the multi-catheter infusion system of FIG. 1.

As shown in FIG. 4A, each catheter 12 includes a multi-orifice distal end 24. The multi-orifice distal end 24 includes a series of perforations or orifices 26 to permit flow laterally out of the catheter 12 i.e., about the sides of the catheter, into the various locations targeted for drug delivery. Preferably, the orifices 26 of the distal end are configured to extend about 0.1-2.0 inches from the most distal end of the catheter.

The orifices 26 can be arranged symmetrically spaced across a periphery of the catheter 12, as shown in FIG. 4A. The number of orifices 26 or specific arrangement of orifices 26 can also vary i.e. be staggeredly positioned, or equally spaced apart. Further, the number, spacing and size of the orifices 26 can vary based on a location, size and type of the wound site being treated.

Figure 4B:
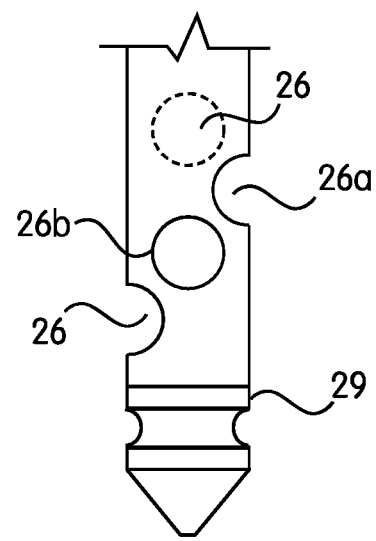
FIG. 4B is another enlarged partial perspective view of a distal end of an individual catheter of the multi-catheter infusion system of FIG. 1 in accordance with another aspect of the present embodiment.

For example, in accordance with an aspect of the present embodiment as shown in FIG. 4B, the orifices 26 can be positioned about the distal end of the catheter so as to be spirally arranged. In this configuration each opening of an orifice spans a circumference of the catheter partially overlapping an adjacent orifice thereby allowing for uniform coverage of fluid dispersion in a radial direction. That is e.g., the circumferential span of orifice 26*a* overlaps the circumferential span of orifice 26*b*. This overlap is continued throughout the spiral arrangement so that 360° of circumferential coverage by the orifices is achieved.

The orifices 26 are preferably circular in shape, but can alternatively be configured in other suitable shape e.g., ovular, square, triangular, trapezoidal, parallelogram, and other irregular shapes. They can also vary in size and number of orifices. However, the number of orifices should be sufficient to achieve a desired elution rate.

Referring back to FIG. 4A, the distal end of each of the plurality of catheters 12 includes a needle 28. The needle 28 is preferably hook shaped, but can alternatively be any shaped needle capable of piercing soft tissue for anchoring or securing the distal end of the catheter 12 to a target delivery area of the patient. That is, the needle 28 on each of the plurality of catheters 12 is used to drive through soft tissue at the desired location with a needle driving instrument (not shown) so that the distal end portion of the catheter is anchored in position by soft tissue alone.

The distal end of each of the plurality of catheters 12 includes a closed distal face. The distal end is closed by a plug 29 for sealing off the distal face of the catheter such that fluid flows out of the catheters only through the orifices 26 under uniform pressure or distribution. The plug 29 further prevents debris and tissue from entering each catheter about its distal face.

The plug 29 can be formed out of any suitable material, such as a plastic, an elastomer, silicone, latex and the like. Preferably, the plug is formed out of a rigid plastic for supporting the needle 28 and providing a weakened portion 30 for detaching the needle from the plug, as further discussed below.

The plug 29 includes a weakened portion 30 to allow a user to breakaway or detach the needle from the plug. The weakened portion 30 can be a notch, a slit, a perforation, a scored section and the like. The weakened portion 30 is a portion of the plug that has e.g., a weaker tensile or yield strength, or can fracture and breakaway under a lower applied load compared to the remainder of the plug. This feature allows the user to detach the needle from the plug after anchoring the distal end of the catheter to soft tissue, as further described below.

The plug 29 also includes a cone or cone-like shaped head about which the needle 28 is attached to. The cone shaped head facilitates traversing the distal end of the catheter through soft tissue.

The present invention also provides a method for delivering a drug to a patient. The method includes inserting the multi-catheter infusion system having the cannula 10 and the plurality of catheters 12 extending from the cannula 10 through a patient's skin. The multi-catheter infusion system 5 is implanted in the patient during a surgical procedure at a point immediately before wound closure. Specifically, a predetermined convenient skin exit site is chosen and the guide needle 16 attached to the cannula 10 is passed from the inside of a wound through the skin to the outside in a manner, such that the plurality of catheters 12 are positioned underneath the skin. Thereafter, the guide needle 16 is detached from the cannula 10. After detaching the guide needle 16, the cannula 10 is connected to the universal adapter 18 for connecting the cannula 10 to the drug delivery system 14, as shown in FIG. 2.

The present method further includes positioning each of the plurality of catheters 12 to a predetermined location. The predetermined location being a location determined by the user or based on a set positioning scheme from the wound.

In order to position each of the catheters 12, the distal end of each of the plurality of catheters 12 is set to a desired location by passing the distal end through soft tissue at the desired location. This is accomplished by using a needle driver to drive the needle 28 at the distal end of each catheter 12 through soft tissue at the desired locations. After passing the distal end through soft tissue at the desired location, the needle 28 is detached from each of the plurality of catheters 12, by conventional means such as scissors or the like. Each catheter is then anchored in position by soft tissue only.

Figure 6:
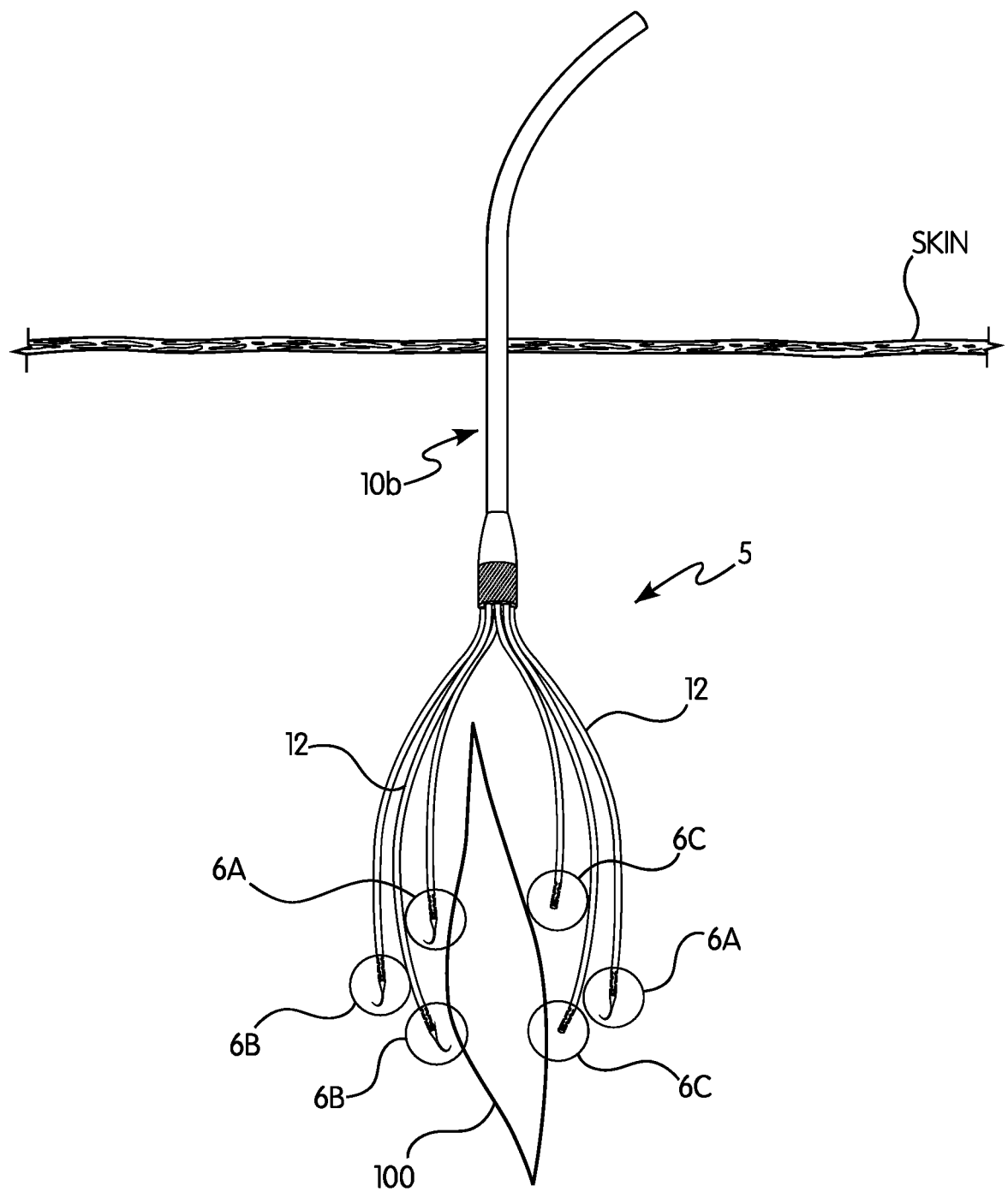
FIG. 6 is an enlarged partial perspective view of the multi-catheter infusion system of FIG. 1 positioned about a wound site of a patient.
Figure 6A:
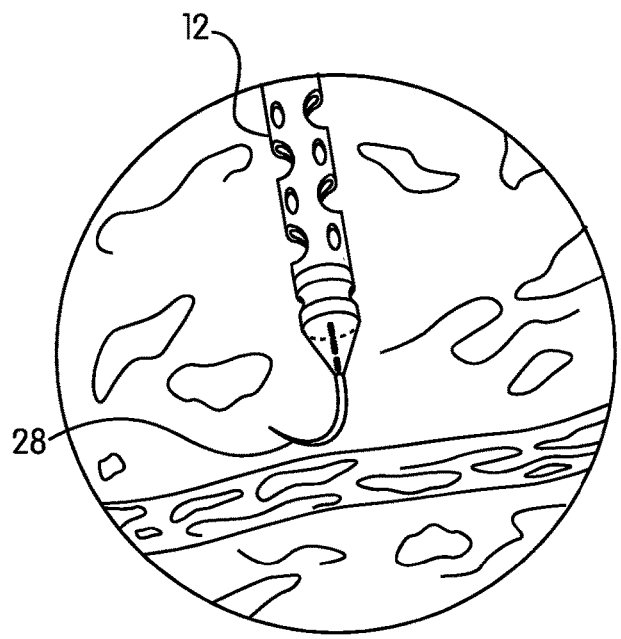
FIGS. 6A-6C are enlarged partial views of various ends of the multi-catheter infusion system of FIG. 6 positioned about a wound site of a patient.
Figure 6B:
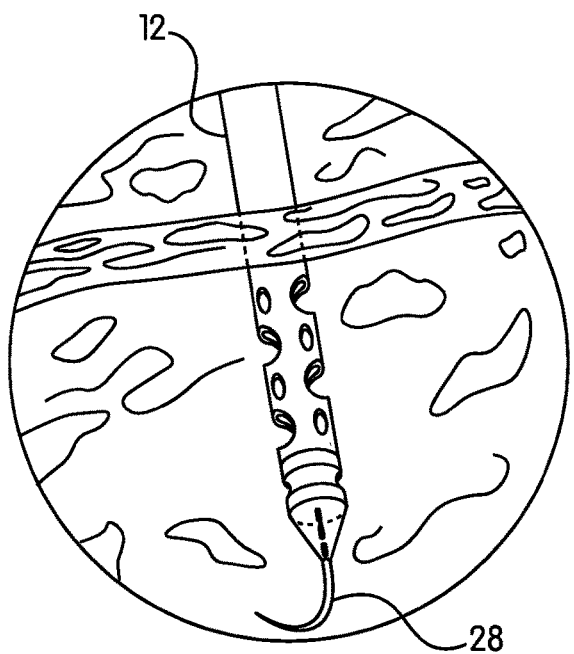
Figure 6C:
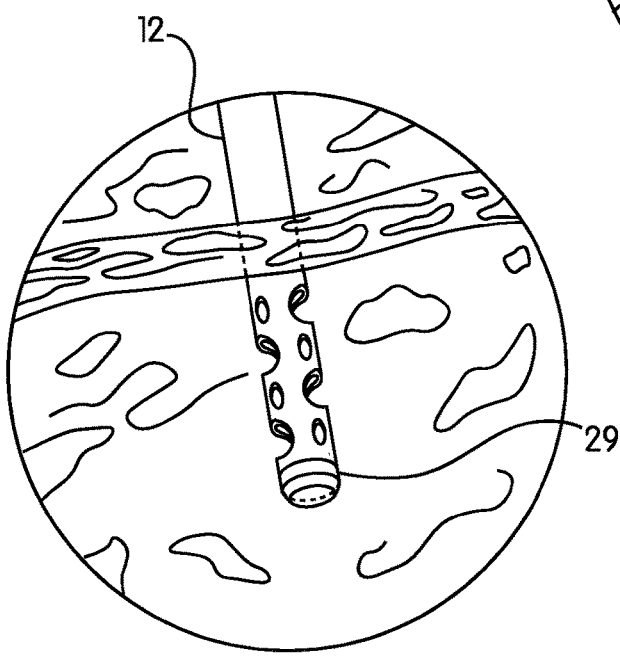

FIG. 6 illustrates the multi-catheter infusion system 5 as applied to a generic wound site 100. The multi-catheter infusion system 5 is shown implanted under the skin in tissue near the wound site 100, with the distal ends of individual catheters in various stages of anchoring as shown in FIGS. 6A-C. FIG. 6A shows a distal end of a catheter 12 prior to being anchored into tissue at a desired location. FIG. 6B illustrates the catheter 12 is shown passed through a tissue portion for anchoring. FIG. 6C illustrates the distal end of the catheter 12 at the desired location with the needle 28 removed.

After all catheters are anchored in position, the wound is closed and the cannula exit site is sterilized in a routine manner. Subsequently, the cannula is connected to the drug delivery system. Drugs are delivered to the patient through the multi-catheter infusion system over an extended period of time. At the conclusion of drug delivery to the patient, the multi-catheter infusion system is withdrawn from the patient by directly pulling the multi-catheter infusion system through the patient's skin. Owing to the tissue anchored ends of the catheters (as shown in FIGS. 6A-C), the multi-catheter infusion system can advantageously be removable easily from the patient.

Figure 5A:
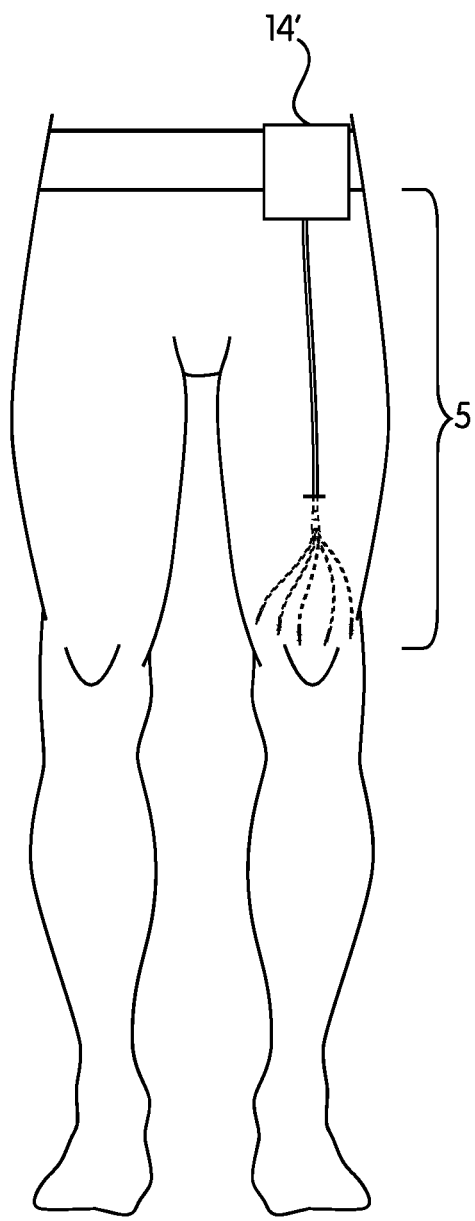
FIGS. 5A and 5B are front and side schematic views of the multi-catheter infusion system applied to a wound site of a patient.
Figure 5B:
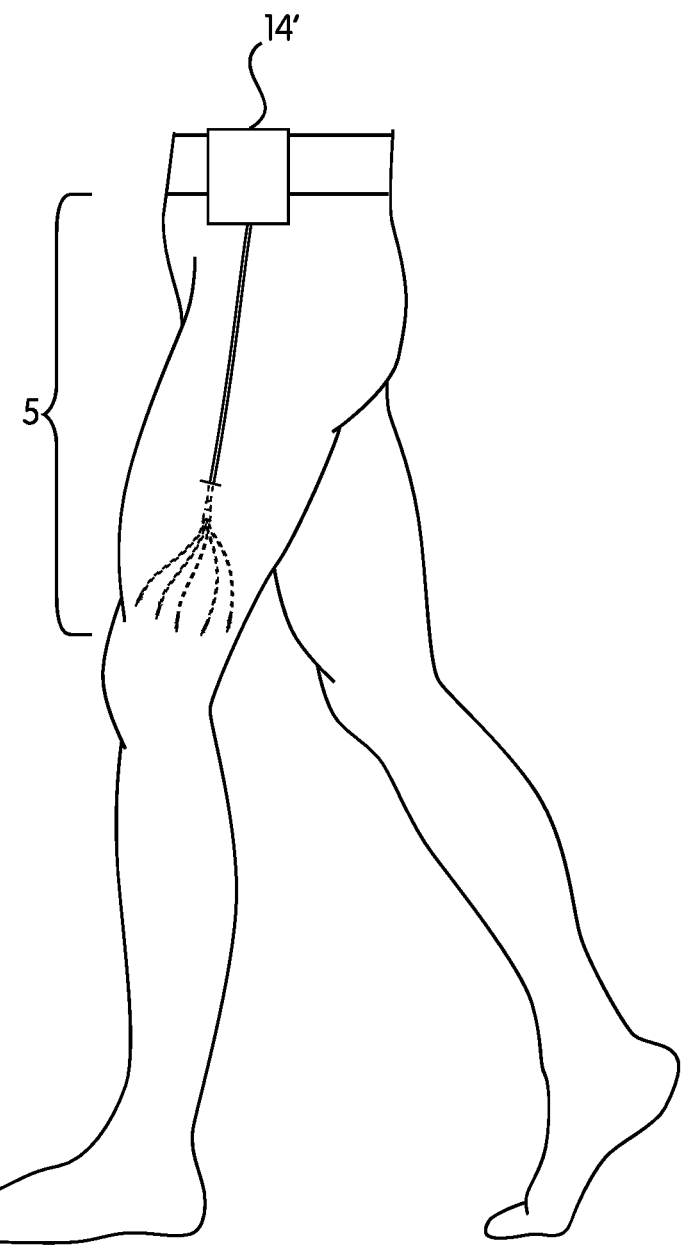

FIGS. 5A and 5B illustrate the multi-catheter infusion system 5 as applied in use to a wound site of a patient, for example, around the patient's knee, and attached to a drug delivery system 14'. The drug delivery system is shown configured as a portable device which may be placed around the patient's waist.

It will be appreciated by those skilled in the art that changes could be made to the embodiments described above without departing from the broad inventive concept thereof. It is to be understood, therefore, that this invention is not limited to the particular preferred embodiments disclosed, but it is intended to cover modifications within the spirit and scope of the present invention as defined by the appended claims.

I claim:

1. A multi-catheter infusion system comprising:
   a cannula including a first end for connecting to a drug delivery system and a second end opposite the first end; and
   a plurality of catheters attached to the second end in fluid communication with the cannula for delivering a drug to a target area of a patient, wherein each catheter includes:
      a multi-orifice distal end,
      a substantially conical plug sealing a distal end of the catheter, and
      a needle extending distally from the plug.

2. The multi-catheter infusion system of claim 1, wherein the second end of the cannula includes a regulator.

3. The multi-catheter infusion system of claim 2, wherein the regulator is a flow regulator or a pressure regulator.

4. The multi-catheter infusion system of claim 2, wherein the plurality of catheters are attached to the second end downstream the regulator.

5. The multi-catheter infusion system of claim 1, wherein the cannula has a cross-sectional diameter greater than an overall diameter of the plurality of catheters.

6. The multi-catheter infusion system of claim 1, wherein the multi-orifices of the distal end extend about 0.1-2 inches.

7. The multi-catheter infusion system of claim 1, wherein the plug includes a weakened portion for detaching the needle from the plug.

8. The multi-catheter infusion system of claim 7, wherein the weakened portion is a notch, a slit, a perforation, or a scored section.

9. The multi-catheter infusion system of claim 1, wherein at least one of the plurality of catheters has a cross-sectional diameter sufficient to draw fluid from the cannula by capillary action.

10. The multi-catheter infusion system of claim 1, wherein the cannula includes a detachable needle for facilitating the positioning of the multi-catheter infusion system.

11. The multi-catheter infusion system of claim 1, wherein the plug is formed out of a plastic, an elastomer, silicone, or latex.

12. A multi-catheter infusion system comprising:
   a cannula including a first end for connecting to a drug delivery system and a second end opposite the first end; and
   a plurality of catheters attached to the second end in fluid communication with the cannula, wherein each catheter includes:
      a multi-orifice distal end,
      a plug,
      a scored portion completely circumscribing a base of the plug and distal to the multi-orifice distal end, and
      a needle distal to the scored portion.

13. The multi-catheter infusion system of claim 12, wherein the scored portion is not in fluid communication with the catheter.

14. The multi-catheter infusion system of claim 12, wherein the scored portion seals a distal facing end of the catheter.

15. The multi-catheter infusion system of claim 12, wherein the needle is curved.

16. A multi-catheter infusion system comprising:
   a cannula including a first end for connecting to a drug delivery system and a second end opposite the first end; and
   a plurality of catheters attached to the second end in fluid communication with the cannula for delivering a drug to a target area of a patient, wherein each catheter includes:
      a multi-orifice distal end,
      a plug having a circumferential weakened portion completely circumscribing a base of the plug and distal to the multi-orifice distal end, and
      pa needle extending from a distal end of the circumferential weakened portion.

17. The multi-catheter infusion system of claim 16, wherein each catheter is a flexible elongated tubular member movable relative to the cannula.

18. A multi-catheter infusion system comprising:
   a cannula including a first end for connecting to a drug delivery system and a second end opposite the first end; and
   a plurality of catheters attached to the second end in fluid communication with the cannula for delivering a drug to a target area of a patient, wherein each catheter includes:
      a multi-orifice distal end, and
      a needle extending distally from a center of a distal end of a plug sealing a distal end of the catheter, the plug having a scored groove completely circumscribing a base of the plug for detaching the needle from the plug.

* * * * *